(12) United States Patent
Oberdoerfer et al.

(10) Patent No.: US 9,335,302 B2
(45) Date of Patent: May 10, 2016

(54) PROBE APPROACH FOR DGS SIZING

(71) Applicant: General Electric Company, Schenectady, NY (US)

(72) Inventors: York Oberdoerfer, North-Rhine-Westphalia (DE); Roman Heinrich Koch, Blankenbach (DE); Wolf-Dietrich Kleinert, Bonn (DE)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 356 days.

(21) Appl. No.: 13/706,531

(22) Filed: Dec. 6, 2012

(65) Prior Publication Data

US 2014/0157903 A1 Jun. 12, 2014

(51) Int. Cl.
*G01N 29/24* (2006.01)
*G01N 29/06* (2006.01)
*G01N 29/26* (2006.01)
*G01N 29/44* (2006.01)
*G01N 29/04* (2006.01)
*G01N 29/28* (2006.01)

(52) U.S. Cl.
CPC .......... *G01N 29/2487* (2013.01); *G01N 29/043* (2013.01); *G01N 29/069* (2013.01); *G01N 29/262* (2013.01); *G01N 29/28* (2013.01); *G01N 29/4463* (2013.01); *G01N 2291/2634* (2013.01)

(58) Field of Classification Search
CPC .................................................... G01N 29/262
USPC ........................................... 73/626, 628, 641
See application file for complete search history.

(56) References Cited

U.S. PATENT DOCUMENTS

| 3,760,345 | A | * | 9/1973 | Hughes ......................... 367/138 |
| 3,919,683 | A | * | 11/1975 | Itamura et al. .................. 73/626 |
| 5,563,346 | A | * | 10/1996 | Bartelt ................ G01S 15/8925 |
| | | | | 600/447 |
| 2010/0031750 | A1 | | 2/2010 | Spencer et al. |
| 2011/0016978 | A1 | | 1/2011 | Kleinert et al. |
| 2011/0138919 | A1 | | 6/2011 | Falter et al. |
| 2011/0247417 | A1 | | 10/2011 | Oberdoerfer et al. |
| 2012/0024067 | A1 | | 2/2012 | Oberdoerfer et al. |
| 2012/0060612 | A1 | | 3/2012 | Kleinert et al. |

FOREIGN PATENT DOCUMENTS

| DE | 102008037173 A1 | 7/2009 |
| DE | 102008027228 A1 | 12/2009 |
| DE | 102008027384 A1 | 12/2009 |

(Continued)

OTHER PUBLICATIONS

International Search Report and Written Opinion from PCT Application No. PCT/US2013/072798 dated Jul. 16, 2014.

(Continued)

*Primary Examiner* — John Chapman, Jr.
(74) *Attorney, Agent, or Firm* — Cooper Legal Group, LLC

(57) ABSTRACT

An ultrasonic detection assembly detects a characteristic in a test object. The ultrasonic detection assembly includes a phased array probe positioned in proximity to a peripheral surface of the test object. The phased array probe includes a plurality of transducer elements. The transducer elements of the phased array probe transmit a sound beam into the test object. The sound beam is movable by the phased array probe within the test object to detect the characteristic. A method of detecting a characteristic in the test object with the ultrasonic detection assembly is also provided.

18 Claims, 4 Drawing Sheets

(56) References Cited

FOREIGN PATENT DOCUMENTS

| EP | 2249152 A2 | | 11/2010 |
| WO | WO 2010/130819 | * | 11/2010 |

OTHER PUBLICATIONS

Partial International Search from PCT/US2013/072798 dated Apr. 9, 2014.

* cited by examiner

PROBE APPROACH FOR DGS SIZING

BACKGROUND OF THE INVENTION

1. Field of the Invention

The present invention relates generally to ultrasonic detection assemblies, and more particularly, to ultrasonic detection assemblies including phased array probes.

2. Discussion of the Prior Art

Ultrasonic detection assemblies are known and used in many different applications. Ultrasonic detection assemblies are used, for example, to inspect a test object and to detect/identify characteristics of the test object, such as corrosion, voids, inclusions, length, thickness, etc. To accurately detect the location of these characteristics within the test object, a straight beam probe was previously used. The straight beam probe emitted a generally straight sound beam into the test object. A wedge was used to provide for inclined sound beams from the straight beam probe into the test object. Multiple different angles (e.g., 3.5°, 7°, 10.5°, 14°, 17.5°, 21°, 24°, etc.) were required to be tested since not all characteristics could be detected with the straight beam probe.

Following these tests, a DGS (distance, gain, size) method was used to determine a size of the characteristic in the test object based on comparing an amplitude of the sound beams for the various angles. The DGS method generally uses straight beam probes generating a rotationally symmetric sound field in the test object. Providing multiple test runs is time consuming, leading to decreased productivity. Further, using differently sized wedges for each of the specified angles (or using multiple probes simultaneously) is difficult, expensive, and time consuming.

Accordingly, it would be beneficial to provide an ultrasonic detection assembly that allows for the transmission of sound beams at multiple different angles to detect characteristics within a test object. Further, it would be beneficial to be able to move the sound beams in a more precise manner without the need for wedges with specific angles (e.g., e.g., 3.5°, 7°, 10.5°, 14°, etc.).

BRIEF DESCRIPTION OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect, an ultrasonic detection assembly for detecting a characteristic in a test object is provided. The ultrasonic detection assembly includes a phased array probe positioned in proximity to a peripheral surface of the test object. The phased array probe transmits a sound beam into the test object. The sound beam is movable by the phased array probe within the test object to detect the characteristic.

In accordance with another aspect, an ultrasonic detection assembly for detecting a characteristic in a test object is provided. The ultrasonic detection assembly includes a phased array probe positioned in proximity to a peripheral surface of the test object. The phased array probe includes a plurality of transducer elements being configured to transmit a sound beam into the test object. The sound beam is movable along at least a two dimensional direction within the test object to detect the characteristic.

In accordance with another aspect, a method of detecting a characteristic in a test object with an ultrasonic detection assembly is provided. The method includes the steps of positioning a phased array probe in proximity to a peripheral surface of the test object. The method also includes the step of transmitting a sound beam from the phased array probe into the test object. The method further includes the step of moving the sound beam within the test object to detect the characteristic.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF THE INVENTION

Figure 1:
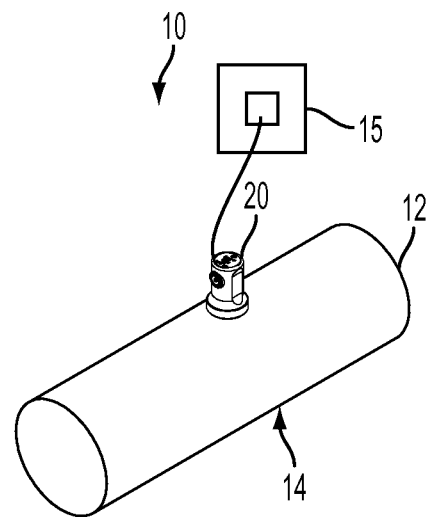
FIG. 1 is a schematic, perspective view of an example ultrasonic detection assembly including a phased array probe detecting a characteristic of a test object in accordance with an aspect of the present invention.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

FIG. 1 illustrates a perspective view of an example ultrasonic detection assembly 10 according to one aspect of the invention. The ultrasonic detection assembly 10 is for inspection of an example test object 12 having a characteristic 18 (e.g., void, inclusion, thickness, crack, corrosion, etc.). The ultrasonic detection assembly 10 includes a phased array probe 20 positioned in proximity to a peripheral surface 14 of the test object 12. The phased array probe 20 can detect the characteristic 18 by directing one or more rotationally symmetric (e.g., generally circular) sound beams into the test object 12. To provide improved detection within the test object 12, the phased array probe 20 can move (e.g., steer) the rotationally symmetric sound beams along a variety of directions within the test object 12.

The example test object 12 includes a tubular shaft having a generally cylindrical shape in FIG. 1. The test object 12 extends between opposing ends and can include a solid body (as shown) or a non-solid body (e.g., hollow body, pipe, or the like). It is to be appreciated that the test object 12 is somewhat generically/schematically depicted in FIG. 1 for ease of illustration. Indeed, the test object 12 can include a variety of dimensions, such as by being longer or shorter than as shown, or by having a larger or smaller diameter. Further, the test object 12 is not limited to a pipe-like structure extending along a linear axis, and may include bends, undulations, curves, or the like.

The peripheral surface 14 of the test object 12 provides the generally cylindrical shape. In other examples, the test object 12 includes other non-cylindrical shapes and sizes. For example, the test object 12 could have a non-circular cross-sectional shape, such as by having a square or rectangular cross-section. Still further, the test object 12 may include a tubular shape, conical shape, or the like. The test object 12 is not limited to shafts, pipes, or the like, but instead, could include walls, planar or non-planar surfaces, etc. The test object 12 could be used in a number of applications, including inspection of parts (e.g., generator shafts, etc.), pipeline corrosion monitoring, or the like. As such, the test object 12 shown in FIG. 1 includes only one possible example of the test object.

The ultrasonic detection assembly 10 further includes a controller 15. The controller 15 is somewhat generically/schematically depicted. In general, the controller 15 can include any number of different configurations. In one example, the controller 15 is operatively attached to the phased array probe 20 by means of a wire. In further examples, however, the controller 15 could be in wireless communication with the phased array probe 20. The controller 15 can send and receive information (e.g., data, control instructions, etc.) from the phased array probe 20 through the wire (or wirelessly). This information can be related to characteristics of the test object 12 (e.g., corrosion, wall thickness, voids, inclusions, etc.), characteristics of sound beams transmitted and/or received by the phased array probe 20, or the like. The controller 15 can include circuits, processors, running programs, memories, computers, power supplies, ultrasound contents, or the like. In further examples, the controller 15 includes a user interface, display, and/or other devices for allowing a user to control the ultrasonic detection assembly 10.

Figure 2:
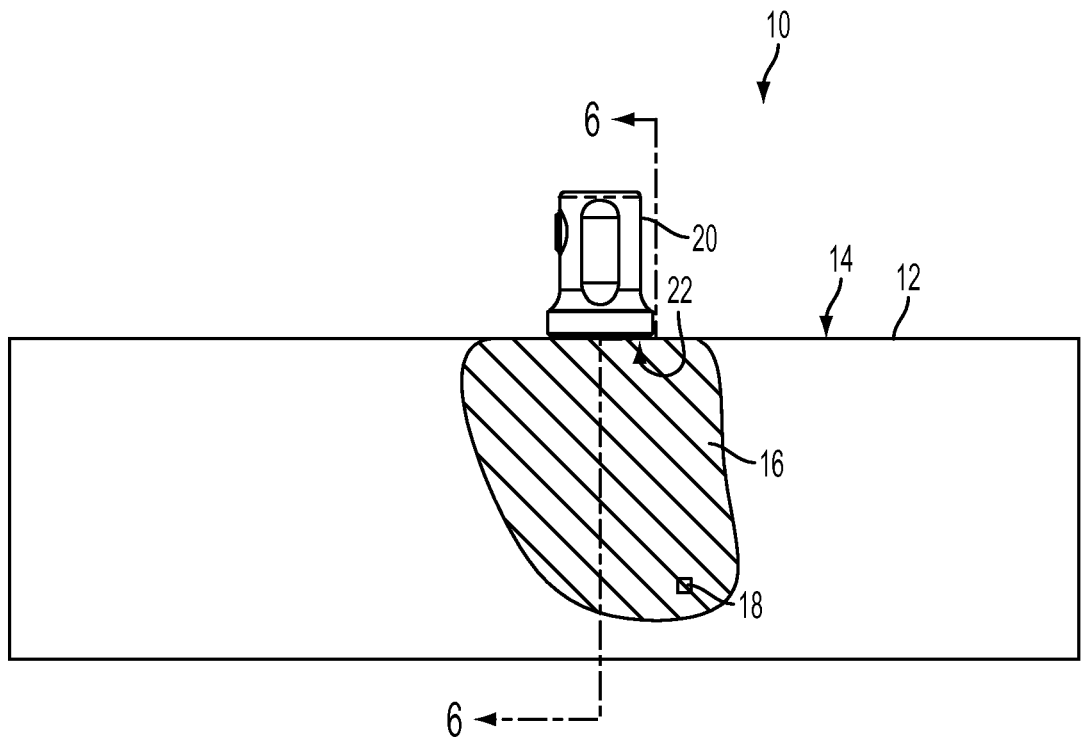
FIG. 2 is a side elevation view of the example ultrasonic sensor assembly that is partially torn open to show an interior portion of the test object.

Turning now to FIG. 2, a partially torn open side elevation view of the test object 12 is shown. The test object 12 includes an interior portion 16. The interior portion 16 is substantially solid, though in further examples, the interior portion 16 could be at least partially hollow and/or include openings therein. The interior portion 16 of the test object 12 could be formed of a number of different materials, including metals (e.g., steel, titanium, etc.), metal alloys, and/or non-metals (e.g., concrete, or the like). It is to be appreciated that while only a portion of the interior portion 16 of the test object 12 is shown (i.e., the torn open portion), the remaining interior portions of the test object 12 can be similar or identical in structure as the interior portion 16 shown in FIG. 2.

The test object 12 can further include a characteristic 18. The characteristic 18 is somewhat generically/schematically depicted, as it is to be appreciated that the characteristic 18 includes a number of possible structures, sizes, shapes, etc. For example, the characteristic 18 includes corrosion, voids, inclusions, defects, cracks, thicknesses, etc. Further, while the characteristic 18 is generically depicted as a quadrilateral shape, the characteristic 18 could likewise include elongated cracks/defects, non-quadrilateral shapes, or the like. It is further appreciated that FIG. 2 depicts one characteristic for illustrative purposes, but in further examples, the characteristic 18 could likewise include a plurality of characteristics. The characteristic 18 may be positioned at any location within the interior portion 16, such as by being closer to or farther from the phased array probe 20, closer to one of the ends of the test object 12, etc.

Turning to the phased array probe 20 of the ultrasonic detection assembly 10, the phased array probe 20 is an elongate, cylindrically shaped probe extending between opposing ends. In further examples, the phased array probe 20 is not limited to the specific structure shown in FIG. 2, and could include any number of different sizes and shapes. The phased array probe 20 is positioned in proximity to the peripheral surface 14 of the test object 12. In one example, the phased array probe 20 is non-movably positioned in proximity to the test object 12, such that the phased array probe 20 is statically held, attached, etc. with respect to the test object 12.

The phased array probe 20 includes an inspection surface 22 disposed at an end of the phased array probe 20. The inspection surface 22 can be substantially planar (as shown), or in further examples, could include bends, curves, or the like to match the shape of the peripheral surface 14. In one example, when the test object 12 has a relatively larger diameter than a length across the inspection surface 22, the inspection surface 22 can be substantially planar such that the inspection surface 22 is in contact with the peripheral surface 14. By being positioned in proximity to the peripheral surface 14, the inspection surface 22 is positioned in contact with the peripheral surface 14. In another example, the inspection surface 22 may be positioned in proximity to the peripheral surface 14 but may not be in contact with the peripheral surface 14. In such an example, the inspection surface 22 may be spaced apart a distance from the peripheral surface 14 and/or may include other structures positioned between (and in contact with) the inspection surface 22 on one side and the peripheral surface 14 on an opposite side.

Figure 3:
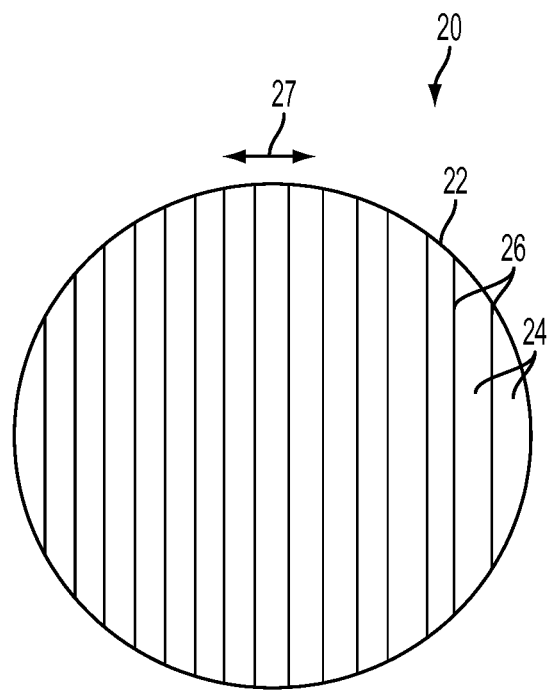
FIG. 3 is an end view of an inspection surface of the phased array probe.

Turning now to FIG. 3, an example of the inspection surface 22 of the phased array probe 20 is shown. The inspection surface 22 includes a generally circular shape associated with a plurality of transducer elements 24. As is generally known, each of the transducer elements 24 includes a piezoelectric crystal. In response to an application of electric current to the transducer elements 24, each of the transducer elements 24 can transmit (e.g., send, convey, etc.) a sound beam in a direction outwardly from the inspection surface 22. Likewise, each of the transducer elements 24 can receive a sound beam, which produces an electrical current in response.

The transducer elements 24 associated with the inspection surface 22 are laterally spaced apart, such as by being linearly segmented. In particular, the transducer elements 24 can be separated by segments 26 that extend generally linearly across the inspection surface 22. The segments 26 extend parallel to each other, such that the transducer elements 24 are arranged to form a linear array. The segments 26 can represent any type of segmentation/separation between the transducer elements 24. For example, the segments 26 can represent cuts, scores, or similar separations manufactured into the inspection surface 22. In another example, the segments 26 represent a space between separately provided transducer elements 24. The segments 26 can be closer together or farther apart, such that the transducer elements 24 could be narrower or wider, respectively.

By providing the transducer elements 24 as being linearly segmented, a sound beam transmitted from the inspection surface 22 can be guided/moved. For example, each of the transducer elements 24 will emit a separate sound beam. The transmission of sound beams from adjacent transducer elements can be delayed (e.g., time shifted), such that a pattern of constructive interference is formed which results in a single sound beam being transmitted at a certain angle. Based on this delay and time shifting, the sound beam from the transducer elements 24 can effectively be moved/guided from the inspection surface 22 and into the test object 12. In the shown example, the sound beam can be moved along a two dimensional direction 27 (represented generically as an arrowhead).

Figure 4:
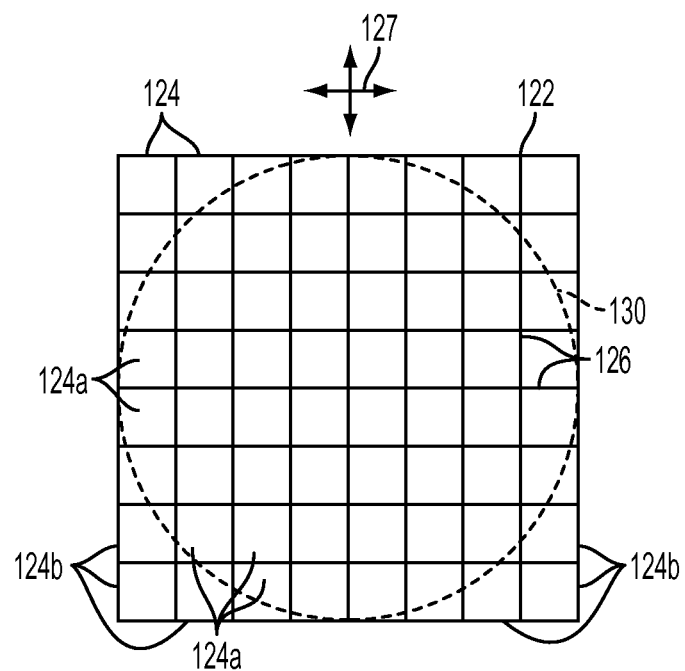
FIG. 4 is an end view of a second example inspection surface of the phased array probe.

Turning now to FIG. 4, a second example of an inspection surface 122 of the phased array probe 20 is shown. In this example, the second inspection surface 122 includes a generally square shape, though other shapes are envisioned. The second inspection surface 122 is associated with a plurality of second transducer elements 124. As is generally known, each of the second transducer elements 124 includes a piezoelectric crystal. As set forth above, each of the second transducer elements 124 can transmit (e.g., send, convey, generate, etc.) a sound beam in a direction outwardly from the second inspection surface 122. Likewise, each of the second transducer elements 124 can receive a sound beam, which produces an electrical current in response.

The second transducer elements 124 associated with the second inspection surface 122 are arranged as a matrix. In particular, the second inspection surface 122 includes a rectangular array of second transducer elements 124 arranged into rows and columns. In the shown example, the matrix includes an 8×8 matrix, with eight rows of second transducer elements 124 and eight columns of second transducer elements 124. Of course, in further examples, the second inspection surface 122 is not limited to including the 8×8 matrix, and could include a matrix of nearly any size (i.e., larger or smaller than as shown). Likewise, the second inspection surface 122 is not limited to including the rectangular array, and could include other quadrilateral shaped arrays, or even non-quadrilateral shaped arrays.

The second transducer elements 124 are separated by segments 126. The segments 126 can extend generally linearly from one side to an opposing second side of the second inspection surface 122. Further, the segments 126 can have a generally consistent spacing between adjacent segments, such that the second transducer elements 124 have substantially identical sizes and shapes (e.g., square shapes). Of course, in further examples, the segments 126 could be oriented in any number of ways. For example, the segments 126 could be angled diagonally across the second inspection surface 122, such that the second transducer elements 124 include non-square shapes.

By providing the second transducer elements 124 in the form of a matrix, a sound beam transmitted from the second inspection surface 122 can be rotationally symmetric. For example, a portion of the second transducer elements 124 (i.e., less than all) can be activated to emit a separate sound beam. In the shown example, active elements 124a will emit sound beams while inactive elements 124b may not emit sound beams. The active elements 124a can form a generally circular shape, indicated as a generally circular grouping 130. The circular grouping 130 of the active elements 124a can be disposed towards the center of the second inspection surface 122. The inactive elements 124b are disposed generally towards the corners of the second inspection surface 122. In the shown example, the active elements 124a can include four transducer elements at a center of each side of the second inspection surface 122. However, in further examples, the circular grouping 130 could be smaller, such that fewer active elements 124a will emit sound beams.

The active elements 124a forming the circular grouping 130 will emit separate sound beams. Similar to the example shown in FIG. 3, the transmission of the sound beams from the active elements 124a can be delayed (e.g., time shifted), such that a pattern of constructive interference is formed which results in a single sound beam being transmitted at a certain angle. Based on this delay and time shifting, the sound beam from the active elements 124a can effectively be moved/guided from the second inspection surface 122 and into the test object 12. In this example, the rotationally symmetric sound beam generated and transmitted by the active elements 124a is moved along a three dimensional direction 127 (represented generically as an arrowhead). As such, the rotationally symmetric sound beam can be moved three dimensionally within the test object 12.

It is to be appreciated that the arrowhead representing the three dimensional direction 127 includes only two perpendicular lines (e.g., first line pointing up/down and second line pointing side to side). However, the movement of the sound beam is not so limited to moving along these directions (e.g., up, down, left, right). Rather, the three dimensional movement of the sound beam includes directions other than those represented with the arrowhead, such as by moving in an angled direction with respect to the perpendicular lines. Indeed, the arrowhead representing the three dimensional direction 127 is merely intended to show that the sound beam emanating from the second inspection surface 122 is not limited to the two dimensional direction 27 of FIG. 3.

Figure 5:
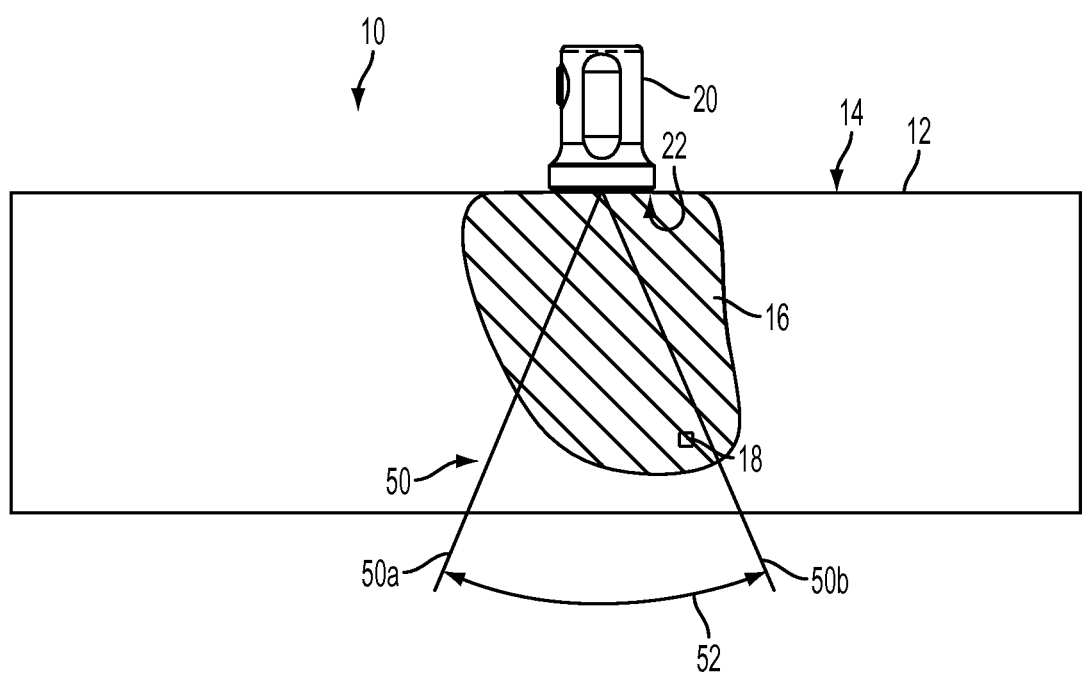
FIG. 5 is a side elevation view of the example ultrasonic sensor assembly similar to FIG. 2 as the phased array probe transmits a rotationally symmetric sound beam into the test object.

Turning now to FIG. 5, the operation of detecting the characteristic in the test object 12 with the ultrasonic detection assembly 10 will now be described. As shown, the phased array probe 20 is positioned in proximity to the test object 12. In particular, the inspection surface 22 (or the second inspection surface 122) of the phased array probe 20 is in contact with the peripheral surface 14 of the test object 12. The test object 12 includes the characteristic 18 positioned within the interior portion 16.

Initially, the phased array probe 20 will generate and transmit a sound beam 50 into the test object 12. The sound beam 50 can include the rotationally symmetric sound beam described above with respect to FIG. 3 or 4. In particular, the phased array probe 20 in FIG. 5 can include either of the inspection surface 22 (FIG. 3) or the second inspection surface (FIG. 4).

The sound beam 50 can initially be in a first sound beam position 50a. The first sound beam position 50a can extend at an angle with respect to the inspection surface 22 into the interior portion 16. It is to be appreciated that the first sound beam position 50a is not specifically limited to the location shown in FIG. 5, and could be located at any position within the interior portion 16. Next, the phased array probe 20 can move the sound beam 50. For example, the transmission of the sound beam 50 from the transducer elements 24 can be delayed (e.g., time shifted), to form a pattern of constructive interference. Based on this delay and time shifting, the sound beam 50 from the inspection surface 22 can be moved/guided within the interior portion 16. In particular, the sound beam 50 can be moved along a direction 52, such that the sound beam 50 will move from the first sound beam position 50a to a second sound beam position 50b.

As the sound beam 50 moves within the test object 12, the sound beam 50 can detect the characteristic 18 within the interior portion 16. In particular, an echo of the sound beam 50 can reflect off the characteristic 18, whereupon the echo is received by the transducer elements 24. Information related to this echo (e.g., amplitude, time of flight, etc.) can be compared with echo signals of known circular disk reflectors. Using a DGS diagram, information related to the characteristic 18 is determinable by comparing the echo amplitude with an array of curves of circular disk reflectors recorded in the DGS diagram. In particular, since the sound beam 50 from either the inspection surface 22 or second inspection surface 122 is rotationally symmetric, the DGS method can still be used since the DGS method depends on a rotationally symmetric sound field.

It is to be appreciated that the first sound beam position 50a and second sound beam position 50b are somewhat generically/schematically represented. Indeed, in further examples, the range along which the sound beam 50 moves is not limited to the range shown in FIG. 5. In one particular example, the sound beam 50 can have a range of approximately 48°, from +24° to −24° with respect to a perpendicular axis extending through a center of the inspection surface 22. Of course, in other examples, the sound beam 50 could have a larger or smaller range. The range of the sound beam 50 can depend on the size of the transducer elements, such that smaller sized transducer elements allow for a larger range.

The sound beam 50 in FIG. 5 is shown to move along the direction 52 that is generally parallel to the axial direction of the test object 12. However, in further examples, rotation of the phased array probe 20 will cause the sound beam 50 to move in other directions that are not parallel to the axial direction of the test object 12. For example, the phased array probe 20 could be rotated 90°, such that the direction 52 of the sound beam 50 is substantially transverse to the axial direction of the test object 12. In other examples, the phased array probe 20 includes the second inspection surface 122. As such, the sound beam 50 is movable along three dimensions.

Figure 6:
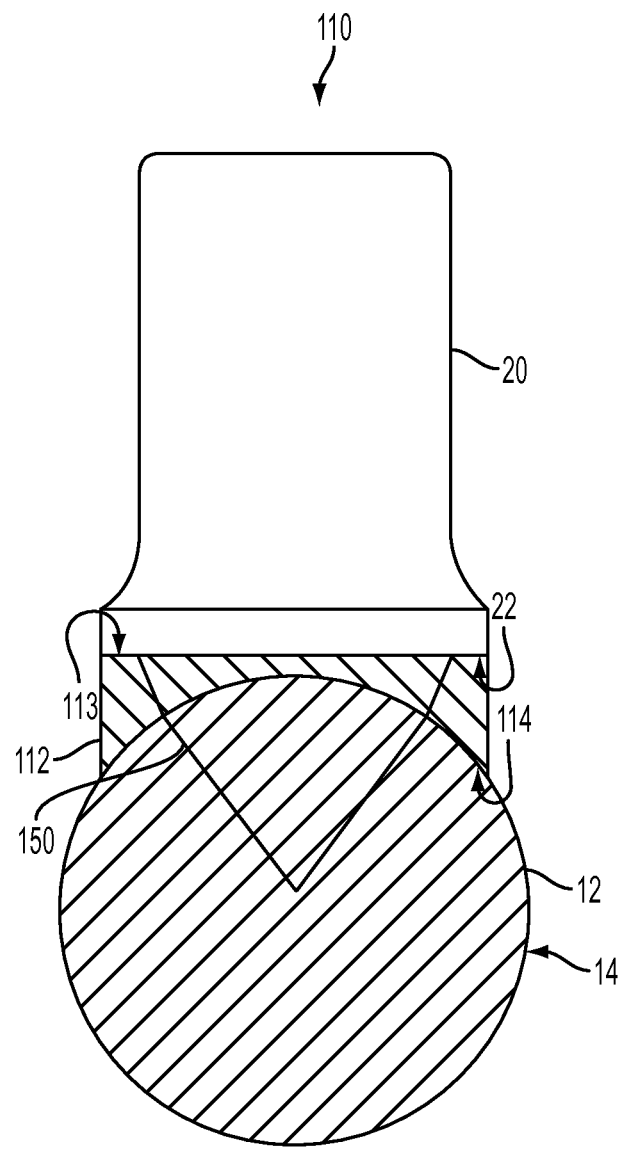
FIG. 6 is a sectional view of a second example ultrasonic sensor assembly along line 6-6 of FIG. 2 including an adjustment structure for positioning the phased array probe in proximity to the test object.

Turning now to FIG. 6, a second example of an ultrasonic detection assembly 110 is shown. FIG. 6 depicts a sectional view along line 6-6 of FIG. 2. In this example, however, the second ultrasonic detection assembly 110 includes an adjustment structure 112. The test object 12 is generally identical to the test object 12 described above with respect to FIGS. 1 to 5. Likewise, the phased array probe 20 is also generally identical to the phased array probe 20 described above with respect to FIGS. 1 to 5. As such, the test object 12 and phased array probe 20 will not be described again with respect to FIG. 6.

The second ultrasonic detection assembly 110 shown in FIG. 6 is a sectional view of FIG. 2. However, the second ultrasonic detection assembly 110 includes the adjustment structure 112 while FIG. 2 does not show the adjustment structure 112. It is to be appreciated that FIG. 6 is similar to FIG. 2, but also includes the adjustment structure 112. In particular, for ease of illustration and to more clearly show portions of the invention, a sectional view of the second ultrasonic detection assembly 110 is shown to include the adjustment structure 112. In operation, the second ultrasonic detection assembly 110 will include the adjustment structure 112 when shown in perspective view.

The second ultrasonic detection assembly 110 includes the adjustment structure 112. The adjustment structure 112 functions to improve contact between the phased array probe 20 and the test object 12. For example, the adjustment structure 112 includes a first surface 113 and a second surface 114. The first surface 113 includes a size and shape that substantially matches a size and shape of the inspection surface 22. For example, the first surface 113 has a generally planar shape that matches the planar shape of the inspection surface 22. In further examples, the first surface 113 could include other, non-planar shapes, that match a non-planar shape of the inspection surface. Indeed, the inspection surface could include either of the inspection surface 22 shown in FIG. 3 or the second inspection surface 122 shown in FIG. 4, with the first surface 113 engaging and contacting either of the inspection surface 22 or second inspection surface 122.

The adjustment structure 112 further includes the second surface 114. The second surface 114 has a size and shape that substantially matches a size and shape of the peripheral surface 14 of the test object 12. For example, the second surface 114 includes a curved, generally concave surface that receives and contacts the peripheral surface 14 of the test object 12. Of course, the second surface 114 is not so limited to the shape shown in FIG. 6. Instead, in further examples, the test object 12 could have a larger or smaller diameter than as shown. To accommodate for this larger or smaller diameter, the second surface 114 could have a greater or lesser degree of concavity, such that the second surface 114 will receive the test object 12.

The adjustment structure 112 could include any number of materials. In one example, the adjustment structure 112 includes an acrylic material, such as polymethyl methacrylate (e.g., Plexiglass®) or the like. The adjustment structure 112 can be clear or opaque, such that a sound beam 150 can pass through the adjustment structure 112.

The phased array probe 20 will transmit the sound beam 150 from the inspection surface 22 and into the test object 12. The sound beam 150 can pass through the adjustment structure 112, by entering through the first surface 113 and then exiting through the second surface 114. The adjustment structure 112 can have a certain influence on the sound beam 150 due to refraction. In particular, as shown in FIG. 6, the sound beam 150 can change directions by passing through the adjustment structure 112. The influence on the sound beam 150 by the adjustment structure 112 could be larger or smaller than as shown, such that the refraction of the sound beam 150 could be more or less severe in further examples. Accordingly, this refraction of the sound beam 150 can be compensated for by knowing the characteristics of the adjustment structure 112, including dimensions (thickness, concavity, etc.), type of material, etc. As such, the sound beam 150 can be moved in a similar manner as described above with respect to FIG. 5 while compensating for refraction due to the adjustment structure 112.

Providing the adjustment structure 112 allows for enhanced coupling of the phased array probe 20 and the test object 12. In examples in which the test object 12 has a relatively small diameter as compared to a size of the inspection surface 22, the adjustment structure 112 is provided to reduce gaps, spaces, etc. between the inspection surface 22 and the test object 12. Without the adjustment structure 112, these gaps, spaces, etc. may exist at edges of the inspection surface 22. The sound beam may be distorted or less effective by traveling from the inspection surface 22, through the gap, space, etc., and then into the test object 12. By including the adjustment structure 112, the sound beam 150 may no longer need to travel through such gaps, and instead can pass through the adjustment structure 112 at positions where the inspection surface 22 and peripheral surface 14 are not in contact (or not adjacent each other).

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. An ultrasonic detection assembly for detecting a characteristic in a test object, the ultrasonic detection assembly including:
   a phased array probe positioned in proximity to a peripheral surface of the test object, the phased array probe including a plurality of adjacent transducer elements collectively configured to provide an inspection surface extending substantially parallel to a direction along which the test object extends, each transducer being operatively configured to emit a respective beam into the test object so as to provide a pattern of constructive interference such that the phased array probe is providing a single, rotationally symmetric sound beam into the test object, the phased array probe being configured to move the sound beam within a range of angles from the phased array probe and bounded by a first beam position extending in a first direction from the phased array probe and a second beam position extending in a second, different direction from the phased array probe within the test object to detect the characteristic.

2. The ultrasonic detection assembly of claim 1, wherein the phased array probe is non-movably positioned in proximity to the peripheral surface of the test object as the sound beam moves within the range of angles from the phased array probe and bounded by the first beam position and the second beam position.

3. The ultrasonic detection assembly of claim 2, wherein the plurality of transducer elements are linearly segmented.

4. The ultrasonic detection assembly of claim 2, wherein the plurality of transducer elements are arranged as a matrix.

5. The ultrasonic detection assembly of claim 4, wherein the matrix includes an 8×8 matrix.

6. The ultrasonic detection assembly of claim 4, wherein within the matrix formed of the plurality of transducer elements, a generally circular grouping formed from the transducer elements is configured to transmit the sound beam.

7. The ultrasonic detection assembly of claim 6, wherein the generally circular grouping formed from the transducer elements is configured to generate and transmit the sound beam, the sound beam being movable along a three dimensional direction within the test object.

8. The ultrasonic detection assembly of claim 1, further including an adjustment structure positioned between the phased array probe and the test object.

9. The ultrasonic detection assembly of claim 8, wherein the adjustment structure includes a first surface that substantially matches a shape of an inspection surface of the phased array probe and an opposing second surface that substantially matches a shape of the peripheral surface of the test object.

10. The ultrasonic detection assembly of claim 1, wherein the sound beams include longitudinal waves.

11. An ultrasonic detection assembly for detecting a characteristic in a test object, the ultrasonic detection assembly including:
a phased array probe positioned in proximity to a peripheral surface of the test object, the phased array probe including a plurality of transducer elements, each transducer being operatively configured to emit a respective beam into the test object so as to provide a pattern of constructive interference such that the phased array probe transmits a single, rotationally symmetric sound beam into the test object, the phased array probe being configured to move the sound beam along at least a two dimensional direction within the test object within a range of angles from the phased array probe and bounded by a first beam position extending in a first direction from the phased array probe and a second beam position extending in a second, different direction from the phased array probe to detect the characteristic;
wherein at least some of the plurality of transducer elements are in contact with the peripheral surface of the test object.

12. The ultrasonic detection assembly of claim 11, wherein the phased array probe is non-movably positioned in proximity to the peripheral surface of the test object as the sound beam moves within the range of angles from the phased array probe and bounded by the first beam position and the second beam position.

13. The ultrasonic detection assembly of claim 11, wherein the plurality of transducer elements are linearly segmented.

14. The ultrasonic detection assembly of claim 11, wherein the plurality of transducer elements are arranged as a matrix.

15. The ultrasonic detection assembly of claim 14, wherein within the matrix formed of the plurality of transducer elements, a generally circular grouping formed from the transducer elements are configured to transmit the sound beam.

16. The ultrasonic detection assembly of claim 15, wherein the generally circular grouping formed from the transducer elements is configured to generate and transmit the sound beam, the sound beam being movable along a three dimensional direction within the test object.

17. A method of detecting a characteristic in a test object with an ultrasonic detection assembly, the method including the steps of:
positioning a phased array probe in proximity to a peripheral surface of the test object including providing the phased array probe to include a plurality of adjacent transducer elements collectively configured to provide an inspection surface extending substantially parallel to a direction along which the test object extends, each transducer being operatively configured to emit a respective beam into the test object so as to provide a pattern of constructive interference, an inspection surface of the phased array probe extending substantially parallel to a direction along which the test object extends;
transmitting a sound beam from the phased array probe into the test object, including emitting beams from transducers so as to provide the constructive interference and so that the sound beam from the phased array probe is a single, rotationally symmetric sound beam; and
moving the sound beam within the test object within a range of angles from the phased array probe and bounded by a first beam position extending in a first direction from the phased array probe and a second beam position extending in a second, different direction from the phased array probe to detect the characteristic.

18. The method of claim 17, the step of moving the sound beam includes moving the sound beam along a three dimensional direction within the test object.

* * * * *